US00PP15433P2

(12) United States Plant Patent
Dekker

(10) Patent No.: US PP15,433 P2
(45) Date of Patent: Dec. 14, 2004

(54) ***BRIGHAMIA* PLANT NAME 'KIRSTEN'**

(50) Latin Name: *Brighamia insignis*
Varietal Denomination: Kirsten

(75) Inventor: Adrianus Cornelis Dekker, Voorhout (NL)

(73) Assignee: Plant Planet, B.V., Voorhout (NL)

( * ) Notice: Subject to any disclaimer, the term of this patent is extended or adjusted under 35 U.S.C. 154(b) by 0 days.

(21) Appl. No.: 10/805,604

(22) Filed: Mar. 20, 2004

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—C. A. Whealy

(57) ABSTRACT

A new and distinct cultivar of *Brighamia* plant named 'Kirsten', characterized by its upright, uniform and compact growth habit; short thick stems; light green-colored leaves; and numerous yellow-colored flowers.

1 Drawing Sheet

Botanical classification/cultivar designation: *Brighamia insignis* cultivar Kirsten.

BACKGROUND OF THE INVENTION

The present Invention relates to a new and distinct cultivar of *Brighamia* plant, botanically known as *Brighamia insignis,* and hereinafter referred to by the name 'Kirsten'.

The new *Brighamia* is a product of a planned breeding program conducted by the Inventor in Schipluiden, The Netherlands. The objective of the program is to create and develop new compact and uniform *Brighamia* cultivars.

The new *Brighamia* originated from a cross-pollination of two unidentified selections of *Brighamia insignis,* not patented, in 1996. The new *Brighamia* was discovered and selected by the Inventor as a flowering plant within the progeny of the stated cross-pollination in a controlled environment in Voorhout, The Netherlands in June, 1999.

Asexual propagation of the new cultivar by meristem culture in Voorhout, The Netherlands since July, 2000, has shown that the unique features of this new *Brighamia* plant are stable and reproduced true to type in successive generations of asexual propagation.

SUMMARY OF THE INVENTION

Plants of the cultivar Kirsten have not been observed under all possible environmental conditions. The phenotype may vary somewhat with variations in environment such as temperature and/or light intensity without, however, any variance in genotype.

The following traits have been repeatedly observed and are determined to be the unique characteristics of 'Kirsten'. These characteristics in combination distinguish 'Kirsten' as a new and distinct cultivar:

1. Upright, uniform and compact growth habit.
2. Short thick stem.
3. Light green-colored leaves.
4. Numerous yellow-colored flowers.

Plants of the new *Brighamia* differ from plants of the parent selections and other selections of *Brighamia* known to the Inventor in growth habit cultivar as plants of the new *Brighamia* are more compact and grow and flower more uniformly.

BRIEF DESCRIPTION OF THE PHOTOGRAPHS

The accompanying colored photographs illustrate the overall appearance of the new cultivar, showing the colors as true as it is reasonably possible to obtain in colored reproduction of this type. Colors in the photographs may differ from the color values cited in the detailed botanical description which accurately describe the colors of the new *Brighamia.*

The photograph at the top of the sheet comprises a close-up view of a typical flower and flower buds of 'Kirsten'.

The photograph at the bottom of the sheet comprises a side perspective view of a typical plant of 'Kirsten' grown in a container.

DETAILED BOTANICAL DESCRIPTION

In the following description, color references are made to The Royal Horticultural Society Colour Chart, 2001 Edition, except where general terms of ordinary dictionary significance are used. Plants used for the above-mentioned photographs and botanical description were grown in Voorhout, The Netherlands in a glass-covered greenhouse in containers during the summer and fall. During the production of the plants, day temperatures were about 20° C. and night temperatures were about 18° C. Plants are used for the aforementioned photographs and following description were about two years old.

Botanical classification: *Brighamia insignis* cultivar Kirsten.

Parentage:

*Female, or seed, parent.*—Unidentified selection of *Brighamia insignis,* not patented.

*Male, or pollen, parent.*—Unidentified selection of *Brighamia insignis,* not patented.

Propagation:

*Type.*—By meristem culture.

*Time to initiate roots.*—About two weeks at 18° C.

*Time to develop roots.*—About eight weeks at 18 to 20° C.

*Root description.*—Fibrous and freely branching.

Plant description:

*Form.*—Upright, uniform and compact growth habit; flattened globular on a short, thick stem.

*Vigor.*—Moderately vigorous to slow-growing.

*Plant height, soil level to top of plant plane.*—About 37 cm.

*Plant width.*—About 41 cm.

*Stem description.*—Quantity: Usually one main stem per plant. Length: About 18 cm. Diameter: Towards the base, about 6.5 cm; towards the apex, about 2.8 cm. Internode length: About 2 mm. Texture: Glabrous; slightly rough; succulent. Strength: Very strong. Color: 191A to 191D.

*Foliage description.*—Arrangement: Alternate, simple; sessile. Quantity: About 40 leaves per plant. Length: About 17 cm. Width: About 7.8 cm. Shape: Obovate. Apex: Rounded to retuse. Base: Cuneate. Margin: Entire. Texture, upper and lower surfaces: Smooth, glabrous; leathery. Venation pattern: Pinnate. Color: Developing foliage, upper surface: 144B to N144C. Developing foliage, lower surface: 144B. Fully expanded foliage, upper surface: 144A to 143B. Fully expanded foliage, lower surface: 143C. Venation, upper and lower surfaces: 145C.

Flower description:

*Flower type and habit.*—Single salverform flowers arranged in axillary corymbs. Flowers face mostly outward. Flowers persistent.

*Fragrance.*—None.

*Natural flowering season.*—Continuously flowering from October until December in The Netherlands.

*Quantity.*—Freely flowering, about three flowers per corymb and about 26 flowers and flower buds per plant.

*Flower longevity on the plant.*—About two weeks.

*Inflorescence height.*—About 22 cm.

*Inflorescence diameter.*—About 15 cm.

*Flower diameter.*—About 4.7 cm.

*Flower depth (height).*—About 13.5 mm.

*Flower buds.*—Length: About 12.5 cm. Diameter: About 1.5 cm. Shape: Broadly ovate with a elongated tube. Color: 150D; tube, 145A to 145B.

*Tepals.*—Quantity per flower: About five; fused tubular corolla. Length: About 12.8 cm. Width: About 1.1 cm. Lobe shape: Elliptic. Apex: Acute. Margin: Finely and irregularly crenate. Texture, upper and lower surfaces: Smooth; glabrous; slightly rugose. Color: When opening and fully opened, upper surface: 4B to 5C. When opening and fully opened, lower surface: 150D.

*Peduncles.*—Length: About 7.3 cm. Diameter: About 4 mm. Angle: About 40 to 75° from vertical. Strength: Moderate. Color: 145A to 145B.

*Pedicels.*—Length: About 3.2 cm. Diameter: About 3 mm. Angle: Erect to about 25° from vertical. Strength: Moderate. Color: 145A to 145B.

*Reproductive organs.*—Androecium: Stamens per flower: About five. Anther shape: Flattened oblong. Anther length: About 1 cm. Anther color: 145C to 145D. Pollen amount: Abundant. Pollen color: 3C. Gynoecium: Quantity of pistils per flower: One. Pistil length: About 10 cm. Stigma shape: Club-shaped. Stigma color: 145B. Style length: About 9.7 cm. Style color: 145B to 145C. Ovary color: 145A to 145B.

*Seeds/fruits.*—Seed and fruit development has not been observed.

Disease/pest resistance: Under commercial production conditions, plants of the new *Brighamia* have not been noted to be resistant to pathogens or pests common to *Brighamia*.

Temperature tolerance: Plants of the new *Brighamia* have been observed to tolerate temperatures from 12 to 35° C. in Schipluiden, The Netherlands.

It is claimed:

1. A new and distinct cultivar of *Brighamia* plant named 'Kirsten', as illustrated and described.

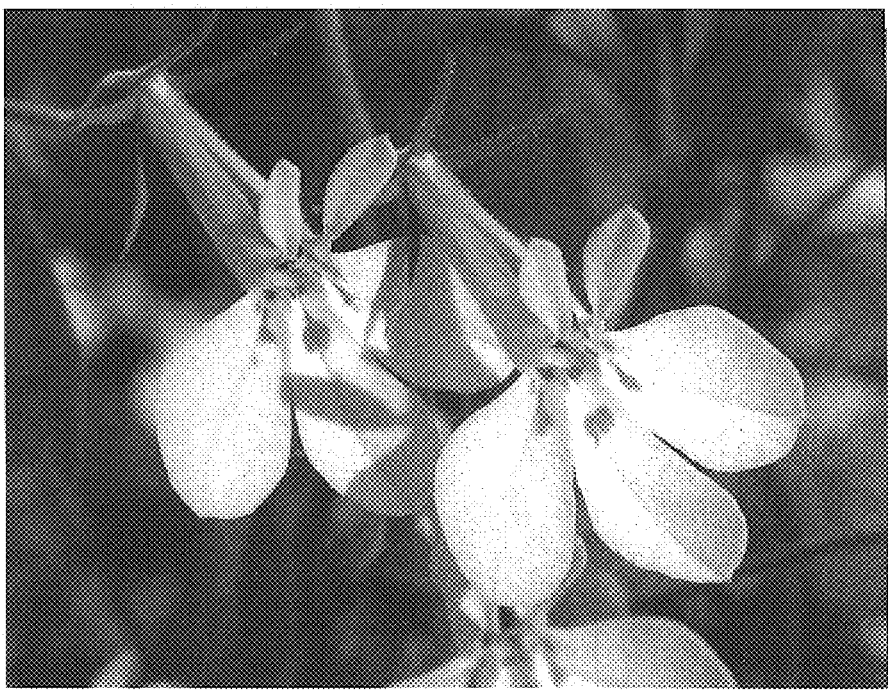
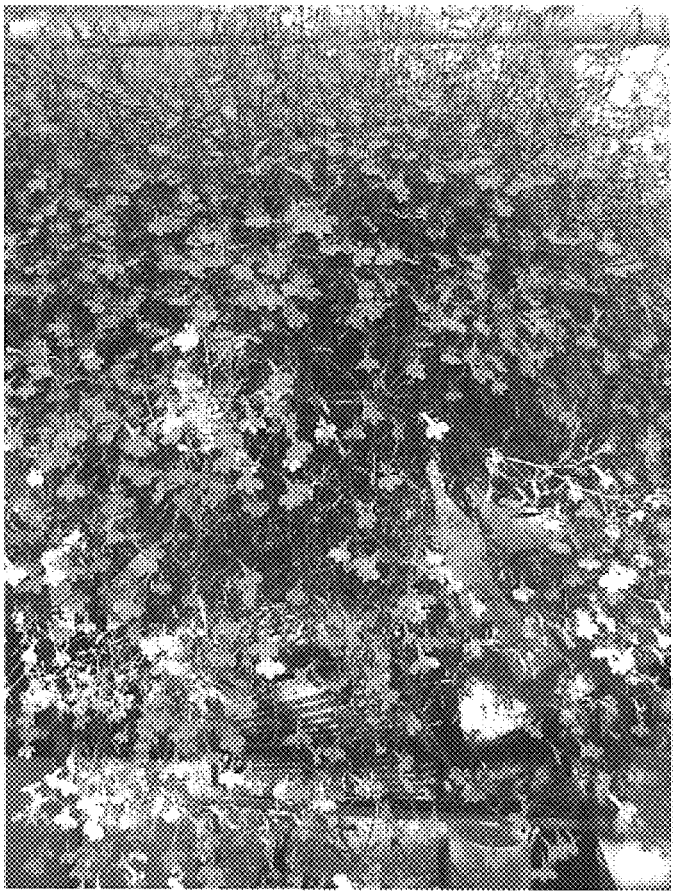

* * * * *